(12) United States Patent
Zhong et al.

(10) Patent No.: US 12,425,006 B2
(45) Date of Patent: Sep. 23, 2025

(54) SYNERGISTIC PULSE GENERATION CIRCUIT, GENERATION DEVICE, AND GENERATION METHOD THEREFOR

(71) Applicant: HANGZHOU WKNIFE MEDICAL TECHNOLOGY CO., LTD, Zhejiang (CN)

(72) Inventors: Xinghua Zhong, Zhejiang (CN); Long Wang, Zhejiang (CN); Ke Yang, Zhejiang (CN)

(73) Assignee: HANGZHOU WKNIFE MEDICAL TECHNOLOGY CO., LTD., Zhejiang (CN)

( * ) Notice: Subject to any disclaimer, the term of this patent is extended or adjusted under 35 U.S.C. 154(b) by 24 days.

(21) Appl. No.: 18/681,034

(22) PCT Filed: Aug. 11, 2022

(86) PCT No.: PCT/CN2022/111828
§ 371 (c)(1),
(2) Date: Feb. 2, 2024

(87) PCT Pub. No.: WO2023/016520
PCT Pub. Date: Feb. 16, 2023

(65) Prior Publication Data
US 2024/0275367 A1 Aug. 15, 2024

(30) Foreign Application Priority Data

Aug. 11, 2021 (CN) .................. 202110921259.X
Aug. 11, 2021 (CN) .................. 202110921262.1

(51) Int. Cl.
*H03K 3/353* (2006.01)
*A61B 18/12* (2006.01)
(Continued)

(52) U.S. Cl.
CPC ......... *H03K 3/353* (2013.01); *A61B 18/1206* (2013.01); *A61B 2017/00176* (2013.01);
(Continued)

(58) Field of Classification Search
CPC ........... H03K 3/353; H03K 3/57; H03K 3/017
See application file for complete search history.

(56) References Cited

U.S. PATENT DOCUMENTS 7,301,250 B2 * 11/2007 Cassel ..................... H03K 3/57
307/106
7,989,987 B2 * 8/2011 McDonald .............. H03K 3/57
307/106
(Continued)

FOREIGN PATENT DOCUMENTS

CN 103446667 A 12/2013
CN 109124759 A 1/2019
(Continued)

OTHER PUBLICATIONS

Office Action and search report issued on Oct. 26, 2024 for the corresponding Chinese Patent Application No. 202110921259.X and its English machine translation.
(Continued)

*Primary Examiner* — Sibin Chen
(74) *Attorney, Agent, or Firm* — Ladas & Parry, LLP (57) ABSTRACT

A synergistic pulse generation circuit comprises a first power supply, a first pulse generation module electrically connected to the first power supply, a second power supply, and a second pulse generation module electrically connected to the second power supply. The first pulse generation module comprises n stages of first pulse generation units, each of which is configured to receive electrical energy provided by the first power supply and store same, so that x of the first pulse generation units receiving a first control
(Continued)

signal discharge to form a first pulse applied to a load. The second pulse generation module comprises m stages of second pulse generation units, each of which is configured to receive electrical energy provided by the second power supply and store same, so that y of the second pulse generation units receiving a second control signal discharge to form a second pulse applied to the load.

18 Claims, 3 Drawing Sheets

(51) Int. Cl.
*A61B 17/00* (2006.01)
*A61B 18/00* (2006.01)

(52) U.S. Cl.
CPC .............. *A61B 2017/0019* (2013.01); *A61B 2018/00577* (2013.01)

(56) References Cited

U.S. PATENT DOCUMENTS

| | | | |
|---|---|---|---|
| 2006/0002050 A1* | 1/2006 | Kichline, Jr. | H03K 3/57 361/160 |
| 2017/0246455 A1 | 8/2017 | Athos et al. | |

FOREIGN PATENT DOCUMENTS

| | | | |
|---|---|---|---|
| CN | 109124760 | A | 1/2019 |
| CN | 110071707 | A | 7/2019 |
| CN | 211300301 | U | 8/2020 |
| CN | 112540221 | * | 3/2021 |
| CN | 112540221 | A | 3/2021 |
| CN | 113098448 | A | 7/2021 |
| CN | 113616312 | A | 11/2021 |
| CN | 113648053 | A | 11/2021 |
| CN | 113824431 | A | 12/2021 |
| CN | 114362725 | A | 4/2022 |
| JP | 2006-135947 | A | 5/2006 |
| JP | 2008011595 | A | 1/2008 |
| JP | 2012-120017 | A | 6/2012 |
| WO | 2017014368 | A1 | 1/2017 |

OTHER PUBLICATIONS

Extended European Search Report issued on Oct. 14, 2024 for the corresponding European Patent Application No. 22855500.9.
International Search Report, International Application No. PCT/CN2022/111828, mailed Oct. 25, 2022, with machine English translation provided by WIPO and by applicant's foreign counsel.
Written Opinion of the International Searching Authority in International Application No. PCT/CN2022/111828, mailed Oct. 25, 2022, with machine English translation provided by WIPO.
Office action from corresponding Japanese Patent Application No. 2024506823 dated Feb. 4, 2025, and its machine English translation by Google Translate.
Office action from corresponding Chinese Patent Application No. 202110921259.X dated May 15, 2025 with search report.
Xinjie Yu, et al., Discussion on the discharging effects of two STRETCH meat grinder modules with different triggering delays, 2014 17th International Symposium on Electromagnetic Launch Technology (EML), Jul. 31, 2014, China.
Yilin Wang, et al., "Development of All-solid-state Pulse Generator for Generating Synergistic Nanoseconds/ Microseconds Pulses," High Voltage Engineering, vol. 46, No. 11: 4061-4068, Nov. 30, 2020, China, and English abstract.

* cited by examiner

SYNERGISTIC PULSE GENERATION CIRCUIT, GENERATION DEVICE, AND GENERATION METHOD THEREFOR

CROSS-REFERENCE TO RELATED APPLICATIONS

The present application is the US national phase application of PCT application No. PCT/CN2022/111828 filed on Aug. 11, 2022, which claims priorities to Chinese Patent Application No. CN 202110921259.X entitled "Synergistic pulse generation circuit, generation apparatus, and generation method therefor" and Chinese Patent Application No. CN 202110921262.1 entitled "Synergistic pulse generation apparatus and system, and generation method", and the disclosures of the above-mentioned patent applications are incorporated herein by reference in their entireties.

TECHNICAL FIELD

The present application relates to the field of pulse generation and medical instruments, and in particular, the present application relates to a synergistic pulse generation circuit, generation device, and generation method therefor.

BACKGROUND

A pulse power technique is an electrophysical technique of rapidly compressing energy that is slowly stored and has relatively high density, and converting the same or directly releasing the same to a load. At the beginning of development, this technique is mainly applied to the military and defense fields of particle accelerators, electromagnetic pulse weapons, intense laser generators, new weapon researches, etc., facilitating the rapid development of a pulse power technique.

In recent years, with the constant extension of the use of the pulse power technique into fields such as medical treatment, environmental science, plasma science, food processing, electromagnetic compatibility testing, bioengineering, etc., the requirements for a pulse generator constantly change as well.

A traditional pulse generator is generally only capable of generating a pulse signal with a specific width, which cannot meet the complex use requirements for the pulse technique.

SUMMARY

The present application aims to solve at least one aspect of the above technical problems to a certain extent, and provides a synergistic pulse generation circuit, generation device, and generation method therefor, which are used for generating pulses in different width ranges and forming more pulse combinations.

In a first aspect, an embodiment of the present application provides a synergistic pulse generation circuit, which includes a first power supply, a first pulse generation module electrically connected to the first power supply, a second power supply, and a second pulse generation module electrically connected to the second power supply.

The first pulse generation module includes n stages of first pulse generation units, each of which is configured to receive electric energy supplied by the first power supply with a first voltage and store the same, and release the stored electric energy when receiving a first control signal, so that x of the first pulse generation units receiving the first control signal discharge electricity to form a first pulse applied to a load. N is an integer greater than or equal to 1, and x is an integer greater than or equal to 1 and less than or equal to n.

The second pulse generation module includes m stages of second pulse generation units, each of which is configured to receive electric energy supplied by the second power supply with a second voltage and store the same, and release the stored electric energy when receiving a second control signal, so that y of the second pulse generation units receiving the second control signal discharge electricity to form a second pulse applied to the load. M is an integer greater than or equal to 1, and y is an integer greater than or equal to 1 and less than or equal to m.

Output ends of the first pulse generation module and the second pulse generation module are connected to the same load, the second voltage is greater than the first voltage, and a width of the second pulse is less than a width of the first pulse.

In a second aspect, an embodiment of the present application provides a synergistic pulse generation device, which includes:
  the synergistic pulse generation circuit according to the first aspect of the present application; and
  a control module electrically connected to the first pulse generation module and the second pulse generation module, respectively, and configured to generate the first control signal and the second control signal according to input information, transmit the first control signal to the first pulse generation module, and transmit the second control signal to the second pulse generation module.

In a third aspect, an embodiment of the present application provides a synergistic pulse generation method, which is used in the synergistic pulse generation circuit according to the first aspect of the present application, and the method includes:
  n stages of first pulse generation units included in a first pulse generation module receiving electric energy supplied by a first power supply with a first voltage and store the same, and m stages of second pulse generation units included in a second pulse generation module receiving electric energy supplied by a second power supply with a second voltage and store the same, where n is an integer greater than or equal to 1, m is an integer greater than or equal to 1, and the second voltage is greater than the first voltage;
  x of the first pulse generation pulse units receiving a first control signal, and discharging electricity under the control of the first control signal to form a first pulse, where x is an integer greater than or equal to 1 and less than or equal to n;
  y of the second pulse generation units receiving a second control signal, and discharging electricity under the control of the second control signal to form a second pulse, where y is an integer greater than or equal to 1 and less than or equal to m; and applying the first pulse and/or the second pulse to the load, wherein a width of the second pulse is less than a width of the first pulse.

In some embodiments, a time when the second pulse generation units receive the second control signal is different from a time when the first pulse generation units receive the first control signal.

The beneficial technical effects brought about by the technical solutions provided in the embodiments of the present application are as follows: by means of the synergistic pulse generation circuit, generation device, and generation method therefor provided by the embodiments of the present application, the first pulse and/or the second pulse with different widths may be selectively formed, and voltages of the first pulse and the second pulse may be selected, thereby achieving the purpose of apply a combination pulse to a load. When the synergistic pulse generation circuit, generation device, and generation method therefor of the present application are used in an electroablation device for treating tumors, taking the load being tumor cells as an example, the action of a combination pulse is conducive to an improvement in the ablation effect on the tumor cells.

BRIEF DESCRIPTION OF THE DRAWINGS

The above and/or additional aspects and advantages of the present application will become apparent and easily comprehensible from the following description of embodiments in below in conjunction with drawings, in which.

LIST OF REFERENCE NUMERALS

1—First pulse generation module; 11—First pulse generation unit; 111—First storage unit; 112—First switch unit; 113—First cutoff unit;
2—Second pulse generation module; 21—Second pulse generation unit; 211—Second storage unit; 212—Second switch unit; 213—Second cutoff unit;
3—Load;
U1—First power supply; and U2—Second power supply.

DETAILED DESCRIPTION

The present application will be described in detail below. Examples of the embodiments of the present application are shown in the drawings, throughout which, the same or similar reference numbers refer to the same or similar components or components having the same or similar functions. In addition, the detailed description of known techniques will be omitted if unnecessary to the shown features of the present application. The embodiments described below with reference to the drawings are exemplary and are merely used to be illustrative of the present application, but should not be construed as limiting the present application.

It should be understood by the skilled in the art that, unless otherwise defined, all terms (including technical and scientific terms) used herein have the same meaning as commonly understood by those of ordinary skills in the art. It should also be understood that terms, such as those defined in commonly used dictionaries, should be construed as having meanings that are consistent with their meanings in the context of the prior art, and will not be construed in an idealized or overly formal sense unless specifically defined as here.

It should be understood by the skilled in the art that, as used herein, the singular form "a", "an" or "the" may include plural forms as well, unless otherwise stated. It should be further understood that the term "include" used in the specification of the present application specifies the presence of the features, integers, steps, operations, elements and/or components, but does not exclude the presence or addition of one or more of other features, integers, steps, operations, elements, components and/or their combinations.

In recent years, with the constant extension of the use of the pulse power technique into fields such as medical treatment, environmental science, plasma science, food processing, electromagnetic compatibility testing, bioengineering, etc., the requirements for a pulse generator constantly change as well.

Taking the field of medicines as an example, the inventors of the present application have found that, when tumor cell ablation is performed using an electroablation technique, a better ablation effect may be achieved by the combination use of multiple types of pulses having different widths than the use of a single type of pulses in some cases. For example, when a microsecond pulse is applied to tumor cells, although the ablation area is relatively large, the ablation rate for the tumor cells, and particularly for malignant tumor cells having a relatively large aberration, is relatively low; and when a nanosecond pulse is applied to the tumor cells, although the ablation rate is relatively high, the ablation area is relatively small. The ablation effect on the tumor cells may be significantly improved by the combination use of the microsecond or millisecond pulse with the nanosecond pulse. In addition to performing ablation of tumor cells using reversible electropores induced by the nanosecond pulse, it is also possible to further synergistically apply a microsecond or millisecond pulse during an existence duration of irreversible electropores induced by the nanosecond pulse, so that an electric field of the microsecond or millisecond pulse penetrates to reach the interiors of cells using pores of cell membranes, further inducing cell apoptosis, whereby a better ablation effect is achieved than separately using the nanosecond pulse, the microsecond pulse or the millisecond pulse. To generate the above synergistic pulses, a corresponding pulse generation device is required. However, a traditional pulse generator is generally only capable of generating a pulse signal with a specific width, which may not meet the complex use requirements for the pulse technique.

The synergistic pulse generation circuit, generation device and generation method therefor provided by the present application aim to solve at least one aspect of the above technical problems to a certain extent. The technical solutions of the present application, and how the technical solutions of the present application solve the above technical problems will be described below in details with particular embodiments.

Figure 1:
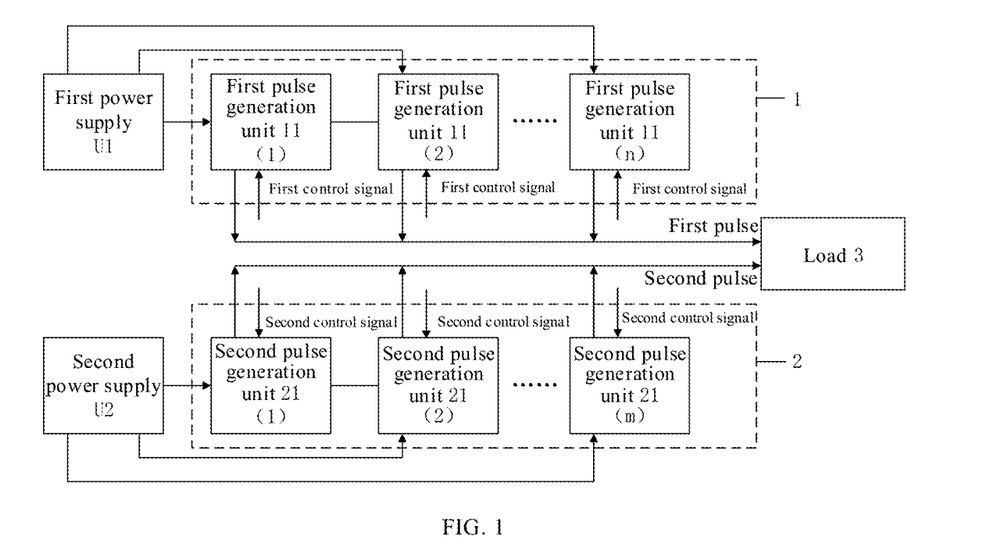
FIG. 1 is a schematic structural diagram of a synergistic pulse generation circuit provided in an embodiment of the present application.

An embodiment of the present application provides a synergistic pulse generation circuit. As shown in FIG. 1, the synergistic pulse generation circuit includes a first power supply U1, a first pulse generation module 1, which is electrically connected to the first power supply U1, a second power supply U2, and a second pulse generation module 2, which is electrically connected to the second power supply U2.

The first pulse generation module 1 includes n stages of first pulse generation units 11, which are configured to receive electric energy supplied by the first power supply U1 with a first voltage and store the same, and release the stored electric energy when receiving a first control signal, so that x of the first pulse generation units 11 receiving the first control signal discharge electricity to form a first pulse applied to a load 3. N is an integer greater than or equal to 1, and x is an integer greater than or equal to 1 and less than or equal to n.

The second pulse generation module 2 includes m stages of second pulse generation units 21, which are configured to receive electric energy supplied by the second power supply U2 with a second voltage and store the same, and release the stored electric energy when receiving a second control signal, so that y of the second pulse generation units 21 receiving the first control signal discharge electricity to form a second pulse applied to the load 3. M is an integer greater than or equal to 1, and y is an integer greater than or equal to 1 and less than or equal to m.

In some embodiments, the second voltage is greater than the first voltage, and the width of the second pulse is less than the width of the first pulse. In some embodiments, the time when the second pulse generation units 21 receive the second control signal is different from the time when the first pulse generation units 11 receive the first control signal.

It should be noted that, theoretically, all the x first pulse generation units 11 receiving the first control signal discharge electricity with the first voltage, but actually, due to the influence of factors such as equivalent impedance of various devices in the pulse generation circuit, the discharge voltage of the first pulse generation units 11 is slightly lower than the first voltage, with the difference between the same and the first voltage being very small. Therefore, the voltage of the first pulse applied to the load 3 may be approximated as x times of the first voltage. Similarly, the voltage of the second pulse applied to the load 3 may be approximated as y times of the second voltage. For ease of illustration, in subsequent embodiments, the actual voltage values of the first pulse generation units 11 and the second pulse generation units 21 during discharge will not be explained and illustrated, and the description will be performed with the first voltage and the second voltage. Based on the above description, the voltage of the first pulse and the voltage of the second pulse may be adjusted by controlling the number of first pulse generation units 11 discharging electricity simultaneously and the number of second pulse generation units 21 discharging electricity simultaneously.

It should be noted that the time when the second pulse generation units 21 receive the second control signal being different from the time when the first pulse generation units 11 receive the first control signal means that the first pulse generation units 11 do not receive the first control signal when the second pulse generation units 21 receive the second control signal, and the second pulse generation units 21 do not receive the second control signal when the first pulse generation units 11 receive the first control signal, that is, the first pulse and the second pulse do not form at the same time, so as to avoid the first pulse and the second pulse from interfering with each other.

Different pulse combinations may be formed by means of setting the first control signal and the second control signal in different manners. For example, in a particular embodiment, a pulse combination includes a plurality of first pulse groups, the time interval between two adjacent first pulse groups is t1, each first pulse group includes a first pulses, and the time interval between two adjacent first pulses is t2. In another particular embodiment, the pulse combination includes a plurality of second pulse groups, the time interval between two adjacent second pulse groups is t3, each second pulse group includes b second pulses, and the time interval between two adjacent second pulses is t4. In still another particular embodiment, the pulse combination includes a plurality of first pulses and a plurality of second pulses. It is possible to alternately apply the first pulses and the second pulses to the load 3. It is also possible to apply the second pulses to the load 3 after all the first pulses have been applied to the load 3, or apply the first pulses to the load 3 after all the second pulses have been applied to the load 3. It is also possible to combine these first pulses into a plurality of first pulse groups and combine these second pulses into a plurality of second pulse groups, and alternately apply the first pulse groups and the second pulse groups to the load 3.

The synergistic pulse generation circuit in the present embodiment may selectively form a first pulse and/or a second pulse with different widths, and may also control voltages of the first pulse and the second pulse, thereby achieving the purpose of applying a combination pulse to the load 3. The widths of the first pulse and the second pulse may be controlled by means of the setting of a control signal. Those skilled in the art may correspondingly configure the voltages of the first power supply and the second power supply and the number of stages of pulse generation units according to different pulse voltage requirements, such that an outputted pulse voltage falls within a required voltage range.

For ease of illustration, a signal outputted by the synergistic pulse generation circuit in the present application may also be referred to as a synergistic pulse or a composite pulse.

Taking the load 3 being a tumor tissue as an example, the action of the composite pulse is conducive to an improvement in the ablation effect on the tumor cells. The first pulse may be a millisecond pulse or a microsecond pulse, and the second pulse may be a nanosecond pulse. Taking a combination of the microsecond pulse and the nanosecond pulse as an example, the voltage of the first pulse may be set to be thousands of volts, whereas the voltage of the nanosecond pulse may be set to be tens of kilovolts. For example, the voltage of the nanosecond pulse is 15 KV. When a second voltage source is selected to be 750 V, an output of 15 KV may be realized by 20 stages of pulse generation units.

In the embodiments above, the optional framework of the synergistic pulse generation circuit is illustrated. In the following embodiments, the structures of the stages of the first pulse generation units 11 and the connection relationship between the stages of the first pulse generation units 11 in the first pulse generation module 1, and the structures of the stages of the second pulse generation units 21 and the connection relationship between the stages of the second pulse generation units 21 in the second pulse generation module 2 will be illustrated in details.

Figure 2:
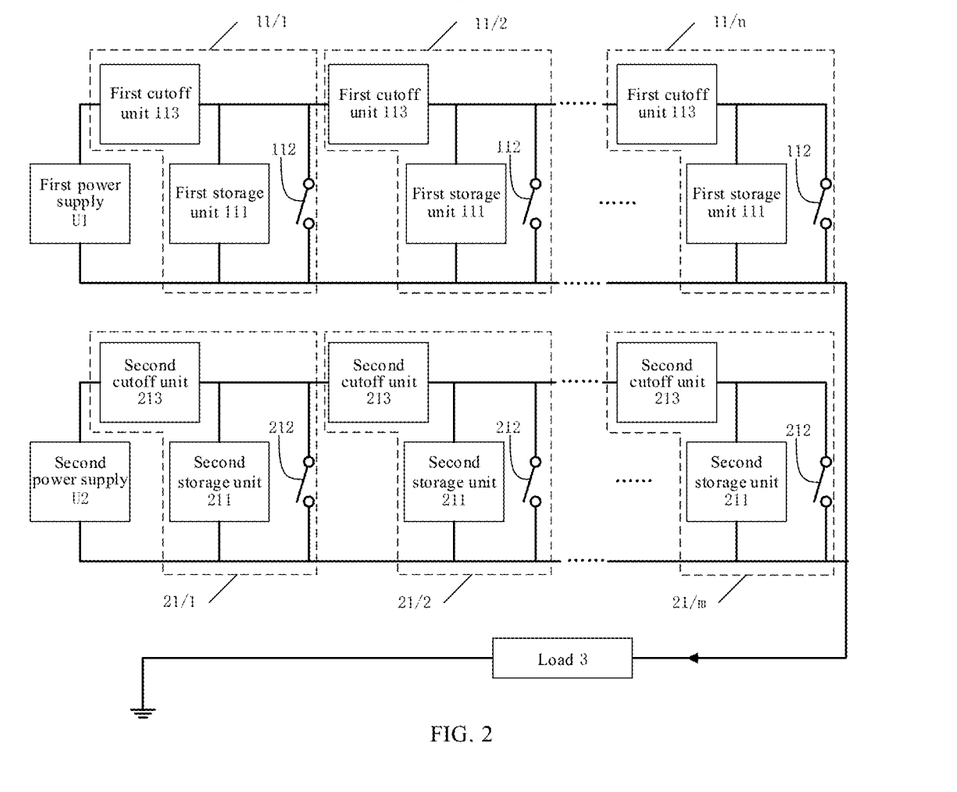
FIG. 2 is a schematic structural diagram of another synergistic pulse generation circuit provided in an embodiment of the present application.

In an optional embodiment, as shown in FIG. 2, in the synergistic pulse generation circuit, the first pulse generation units 11 each includes a first storage unit 111, a first switch unit 112 and a first cutoff unit 113, and the second pulse generation units 21 each includes a second storage unit 211, a second switch unit 212 and a second cutoff unit 213.

As shown in FIG. 2, the first switch units 112 are configured to turn on under the control of the first control signal so that the respective first storage units 111 at the same stages as those of the first switch units 112 receiving the first control signal are connected in series and discharge electricity to form a first pulse. As shown in FIG. 2, each of the first cutoff units 113 is configured to only allow a current to flow from the first power supply U1 to the first pulse generation unit 11 or from the current stage of the first pulse generation unit 11 to the next stage of a first pulse generation unit 11.

Specifically, during discharging, only the first switch units 112 receiving the first control signal are turned on. Moreover, due to a unidirectional cutoff function of the first cutoff units 113, the first storage units 111 in the first pulse generation units 11 receiving the first control signal are connected in series and discharge electricity. The first storage units 111 are equivalent to power supplies during the discharging process, and these power supplies connected in series discharge electricity with the first voltage simultaneously. When x first storage units 111 among n stages of the first storage units 111 are connected in series and discharge electricity, the voltage of the formed first pulse is x times of the first voltage.

As shown in FIG. 2, the second switch units 212 are configured to turn on under the control of the second control signal so that the respective second storage units 211 at the same stages as those of the second switch units 212 receiving the second control signal are connected in series and discharge electricity to form a second pulse. Each of the second cutoff units 213 is configured to only allow a current to flow from the second power supply U1 to the second pulse generation unit 21 or from the current stage of the second pulse generation unit 21 to the next stage of a second pulse generation unit 21.

Specifically, during discharging, only the second switch units 212 receiving the second control signal are turned on. Moreover, due to a unidirectional cutoff function of the second cutoff units 213, the second storage units 211 in the second pulse generation units 21 receiving the second control signal are connected in series and discharge electricity. The second storage units 211 are equivalent to power supplies during the discharging process, and these power supplies connected in series discharge electricity with the second voltage simultaneously. When y second storage units 211 among the m stages of the second storage units 211 are connected in series and discharge electricity, the voltage of the formed second pulse is y times of the second voltage.

As shown in FIG. 2, the first switch units 112 are further configured to turn off when receiving a third control signal, so that stages of first storage units 111 are connected to the first power supply U1 in parallel to receive electric energy supplied by the first power supply U1 and store the same; and the second switch units 212 are further configured to turn off when receiving a fourth control signal, so that stages of second storage units 211 are connected to the second power supply U2 in parallel to receive electric energy supplied by the second power supply U2 and store the same.

Specifically, when the first switch units 112 are in a turn-off state, due to the unidirectional cutoff function of the first cutoff units 113, the stages of the first storage units 111 are connected in parallel and store, with the first voltage, the electric energy supplied by the first power supply U1. Similarly, the stages of the second storage units 211 are also connected in parallel and store, with the first voltage, the electric energy supplied by the first power supply U1.

Figure 3:
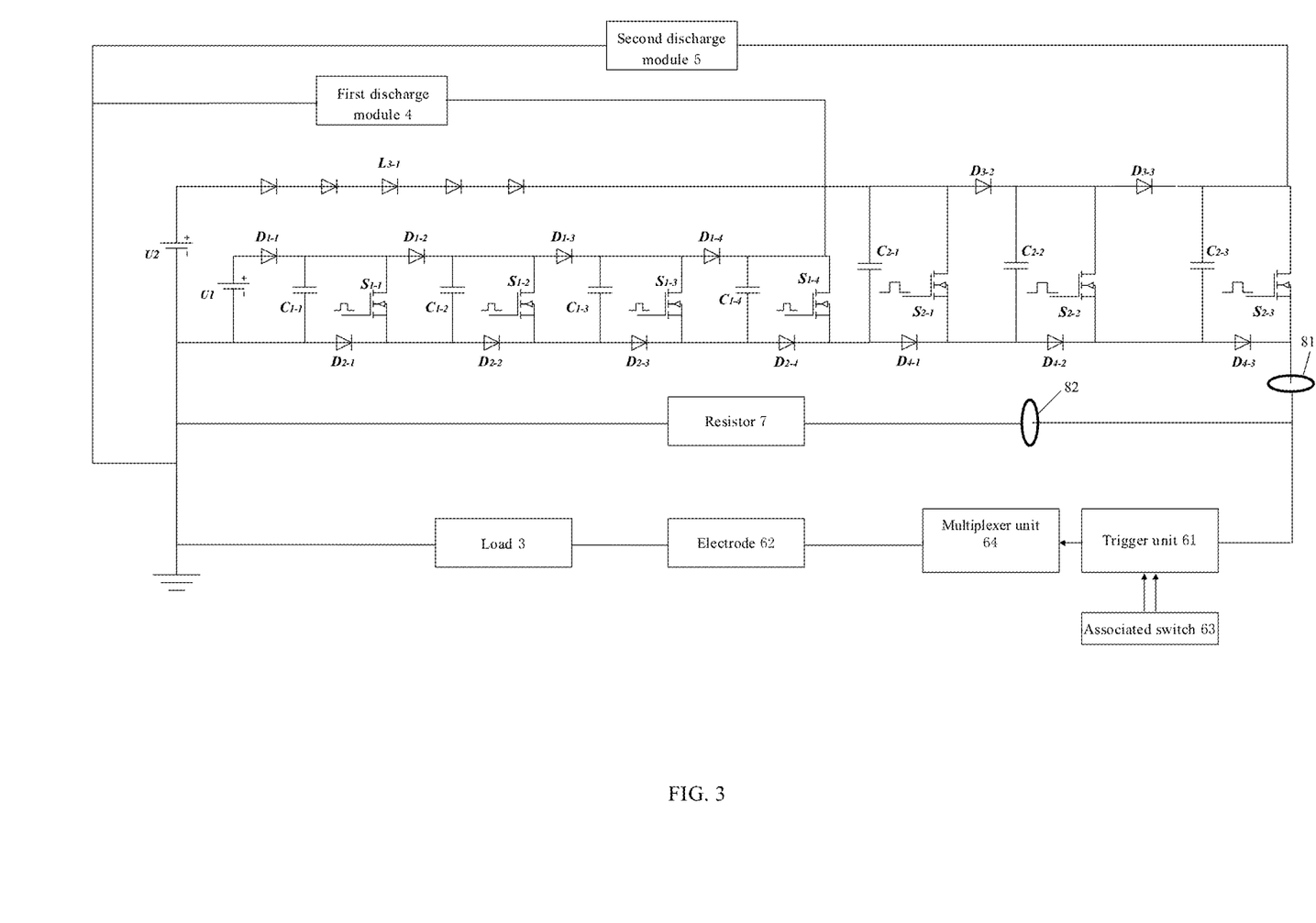
FIG. 3 is a schematic structural diagram of still another synergistic pulse generation circuit provided in an embodiment of the present application.

In a particular embodiment, as shown in FIG. 3, in the synergistic pulse generation circuit, the first cutoff units 113 each includes a first cutoff device and a second cutoff device. A first-stage first cutoff device is electrically connected to a first end of the first power supply U1 and a first end of a first-stage first storage unit 111, respectively; an ith-stage first cutoff device is electrically connected to a first end of an (i−1)th-stage first storage unit 111, a first end of an ith-stage first storage unit 111 and an (i−1)th-stage first cutoff device, respectively; and each stage of a second cutoff device is electrically connected to a second end of the current stage of a first storage unit 111, a second end of the current stage of a first switch and the next stage of a second cutoff device, respectively, and i is an integer greater than or equal to 2.

As shown in FIG. 3, in the synergistic pulse generation circuit, the second cutoff units 213 each includes a third cutoff device and a fourth cutoff device. A first-stage third cutoff device is electrically connected to a first end of the second power supply U2 and a first end of a first-stage second storage unit 211, respectively; a jth-stage third cutoff device is electrically connected to a first end of a (j−1)th-stage second storage unit 211, a first end of a jth-stage second storage unit 211 and a (j−1)th-stage third cutoff device, respectively; and each stage of a fourth cutoff device is electrically connected to a second end of the current stage of a second storage unit 211, a second end of the current stage of a second switch and the next stage of a fourth cutoff device, respectively, and j is an integer greater than or equal to 2.

Furthermore, as shown in FIG. 3, two ends of each stage of the first storage unit 111 are electrically connected to two ends of the first power supply U1, respectively, a control end of each stage of the first switch unit 112 is configured to receive the first control signal, and a first end and a second end of each stage of the first switch unit 112 are electrically connected to a first end of the current stage of the first storage unit 111 and a second end of the next stage of the first storage unit 111, respectively; and two ends of each stage of the second storage unit 211 are electrically connected to two ends of the second power supply U1, respectively, a control end of each stage of the second switch unit 212 is configured to receive the second control signal, and a first end and a second end of each stage of the second switch are electrically connected to a first end of the current stage of the second storage unit 211 and a second end of the next stage of the second storage unit 211, respectively.

In some particular embodiments, the first storage units 111 each includes a first capacitor, and the second storage units 211 each includes a second capacitor. The first switch units each includes a first solid-state switch device, and the second switch units 212 each includes a second solid-state switch. The first cutoff devices each includes a first diode, the second cutoff devices each includes a second diode, the third cutoff devices each includes a third diode, and the fourth cutoff devices each includes a fourth diode. That is, the capacitors are used as the storage units, the solid-state switch devices are used as the switch units, and the diodes are used as the cutoff devices. The solid-state switch devices may be implemented based on a metal-oxide-semiconductor field-effect transistor (MOSFET), an insulated gate bipolar transistor (IGBT) or a crystal triode, etc.

Further referring to FIG. 3, in the synergistic pulse generation circuit, the first pulse generation module 1 includes four stages of the first pulse generation units 11, and the second pulse generation module 2 includes three stages of the second pulse generation units 21, that is, n is equal to 4, and m is equal to 3. It should be noted that this is for an illustrative purpose only, and is not used for limiting the number of stages of the first pulse generation units 11 in the first pulse generation module 1 and the number of stages of the second pulse generation units 21 in the second pulse generation module 2.

As shown in FIG. 3, the first to fourth stages of the first switch units 112, i.e., the first to fourth stages of the first solid-stage switch devices, are respectively a solid-state switch device $S_{1-1}$, a solid-state switch device $S_{1-2}$, a solid-state switch device $S_{1-3}$ and a solid-state switch device $S_{1-4}$. The first to fourth stages of first storage units are respectively a capacitor $C_{1-1}$, a capacitor $C_{1-2}$, a capacitor $C_{1-3}$ and a capacitor $C_{1-4}$. The first to fourth stages of the first cutoff devices are respectively a diode $D_{1-1}$, a diode $D_{1-2}$, a diode $D_{1-3}$ and a diode $D_{1-4}$. The first to fourth stages of the second cutoff devices are respectively a diode $D_{2-1}$, a diode $D_{2-2}$, a diode $D_{2-3}$ and a diode $D_{2-4}$.

As shown in FIG. 3, the first to fourth stages of the second switch units 212, i.e., the first to fourth stages of second triodes, are respectively a solid-state switch device $S_{2-1}$, a solid-state switch device $S_{2-2}$, a solid-state switch device $S_{2-3}$ and a solid-state switch device $S_{2-4}$. The first to fourth stages of the second storage units 211 are respectively a capacitor $C_{2-1}$, a capacitor $C_{2-2}$, a capacitor $C_{2-3}$ and a capacitor $C_{2-4}$. The first to fourth stages of the third cutoff devices are respectively a diode $D_{3-1}$, a diode $D_{3-2}$, a diode $D_{3-3}$ and a diode $D_{3-4}$. The first to third stages of the fourth cutoff devices are respectively a diode $D_{4-1}$, a diode $D_{4-2}$ and a diode $D_{4-3}$.

As shown in FIG. 3, in the synergistic pulse generation circuit, when the first power supply U1 charges the first storage units 111, i.e., the capacitor $C_{1-1}$, the capacitor $C_{1-2}$, the capacitor $C_{1-3}$ and the capacitor $C_{1-4}$, a current flows through the second cutoff devices, i.e., the diode $D_{2-1}$, the diode $D_{2-2}$, the diode $D_{2-3}$ and the diode $D_{2-4}$, and When the second power supply U2 charges the second storage units 211, i.e., the capacitor $C_{2-1}$, the capacitor $C_{2-2}$ and the capacitor $C_{2-3}$, a current flows through the fourth cutoff devices, i.e., the diode $D_{4-1}$, the diode $D_{42}$ and the diode $D_{4-3}$.

As shown in FIG. 3, in the synergistic pulse generation circuit, when the capacitor $C_{1-1}$, the capacitor $C_{1-2}$, the capacitor $C_{1-3}$ and the capacitor $C_{1-4}$ discharge electricity, a current flows through the fourth cutoff devices, i.e., the diode $D_{4-1}$, the diode $D_{4-2}$ and the diode $D_{4-3}$, and when the capacitor $C_{2-1}$, the capacitor $C_{2-2}$ and the capacitor $C_{2-3}$ discharge electricity, the diode $D_{4-1}$, the diode $D_{4-2}$ and the diode $D_{4-3}$ operate in a reverse cutoff state.

The first pulse generation module 1 and the second pulse generation module 2 in the synergistic pulse generation circuit provided by the present embodiment may realize the generation of a composite pulse, and may also reduce the wiring space, i.e., may take a circuit board with a smaller area as a carrier of the synergistic pulse generation circuit in the present embodiment.

As shown in FIG. 3, the first power supply U1 and the second power supply U2 are both constant-voltage power supplies. When the solid-state switch device $S_{1-1}$, the solid-state switch device $S_{1-2}$, the solid-state switch device $S_{1-3}$ and the solid-state switch device $S_{1-4}$ receive a third control signal, the solid-state switch device $S_{1-1}$, the solid-state switch device $S_{1-2}$, the solid-state switch device $S_{1-3}$ and the solid-state switch device $S_{1-4}$ are all in a turn-off state. The diode $D_{1-1}$, the diode $D_{1-2}$, the diode $D_{1-3}$ and the diode $D_{1-4}$, and the diode $D_{2-1}$, the diode $D_{2-2}$ and the diode $D_{2-3}$ all have an unidirectional conduction function, such that the capacitor $C_{1-1}$, the capacitor $C_{1-2}$, the capacitor $C_{1-3}$ and the capacitor $C_{1-4}$ have a parallel connection relationship and are all electrically connected to the first end and the second end of the first power supply U1, i.e., all being electrically connected to the positive electrode and the negative electrode of the first power supply U1. After charging is completed, the potential difference between two ends of each of the capacitor $C_{1-1}$, the capacitor $C_{1-2}$ and the capacitor $C_{1-3}$ is the first voltage.

Similarly, when the solid-state switch device $S_{2-1}$, the solid-state switch device $S_{2-2}$ and the solid-state switch device $S_{2-3}$ all receive a fourth control signal, the capacitor $C_{2-1}$, the capacitor $C_{2-2}$ and the capacitor $C_{2-3}$ have a parallel connection relationship and are all electrically connected to the first end and the second end of the second power supply U2, i.e., all being electrically connected to the positive electrode and the negative electrode of the second power supply U2. After charging is completed, the potential difference between two ends of each of the capacitor $C_{2-1}$, the capacitor $C_{2-2}$ and the capacitor $C_{2-3}$ is the second voltage.

As shown in FIG. 3, when the solid-state switch device $S_{1-1}$, the solid-state switch device $S_{1-2}$, the solid-state switch device $S_{1-3}$ and the solid-state switch device $S_{1-4}$ all receive the first control signal, the solid-state switch device $S_{1-1}$, the solid-state switch device $S_{1-2}$, the solid-state switch device $S_{1-3}$ and the solid-state switch device $S_{1-4}$ are all in a turn-on state. Since the diode $D_{1-1}$, the diode $D_{1-2}$, the diode $D_{1-3}$ and the diode $D_{1-4}$, and the diode $D_{2-1}$, the diode $D_{2-2}$, the diode $D_{2-3}$ and the diode $D_{2-4}$ all have the unidirectional conduction function, the capacitor $C_{1-1}$, the capacitor $C_{1-2}$, the capacitor $C_{1-3}$ and the capacitor $C_{1-4}$ have a serial connection relationship, and the capacitor $C_{1-1}$, the capacitor $C_{1-2}$, the capacitor $C_{1-3}$ and the capacitor $C_{1-4}$ discharge electricity simultaneously, with the discharge voltages all being the first voltage, such that the voltage of the formed pulse is four times of the first voltage.

Similarly, when the solid-state switch device $S_{2-1}$, the solid-state switch device $S_{2-2}$ and the solid-state switch device $S_{2-3}$ all receive the second control signal, the solid-state switch device $S_{2-1}$, the solid-state switch device $S_{2-2}$ and the solid-state switch device $S_{2-3}$ are all in the turn-on state, the capacitor $C_{2-1}$, the capacitor $C_{2-2}$ and the capacitor $C_{2-3}$ have the serial connection relationship, and the capacitor $C_{2-1}$, the capacitor $C_{2-2}$ and the capacitor $C_{2-3}$ discharge electricity simultaneously, with the discharge voltages all being the second voltage, such that the voltage of the formed second pulse is three times of the second voltage.

Furthermore, as shown in FIG. 3, in the synergistic pulse generation circuit, the second to nth stages of the first cutoff devices each includes one first diode, each stage of the second cutoff device includes one second diode, and a reverse breakdown voltage of each of the first diodes and a reverse breakdown voltage of each of the second diodes are both greater than the first voltage. The second to mth stages of the third cutoff devices each includes one third diode, each stage of the fourth cutoff device includes one fourth diode, and a reverse breakdown voltage of each of the third diodes and a reverse breakdown voltage of each of the fourth diodes are both greater than the second voltage. The first-stage first cutoff device includes s first diodes, and s times of the reverse breakdown voltage of each first diode is greater than (n−1) times of the first voltage. The first-stage third cutoff device includes t third diodes, and s times of the reverse breakdown voltage of each third diode is greater than (m−1) times of the second voltage. S is an integer greater than or equal to 1, and t is an integer greater than or equal to 1.

Taking the synergistic pulse generation circuit shown in FIG. 3 as an example, the first pulse generation module 1 includes four stages of the first pulse generation units 11, and the second pulse generation module 2 includes three stages of the second pulse generation units 21. If all the diodes used as the cutoff devices have the same parameters, since the first voltage is less than the second voltage, the second voltage should be taken as a selection basis in order to ensure that all the diodes may normally provide the unidirectional cutoff function. For example, if the second voltage is 1000 V, the reverse breakdown voltage of each diode should be greater than 1000 V.

As shown in FIG. 3, if the first voltage is 200 V, the second voltage is 1000 V and the ground level is 0 V, the reverse breakdown voltage of each diode is 1100 V. During the discharging process of the first pulse generation module, if the solid-state switch device $S_{1-1}$, the solid-state switch device $S_{1-2}$, the solid-state switch device $S_{1-3}$ and the solid-state switch device $S_{1-4}$ are all in the turn-on state, the voltage of the end of the capacitor $C_{1-1}$ that is connected to the positive electrode of the first power supply U1 is 800 V. At this time, the voltage difference between two ends of the diode $D_{1-1}$ is 800 V, and it is thus only necessary to provide one diode $D_{1-1}$. If the solid-state switch device $S_{1-1}$, the solid-state switch device $S_{1-2}$, the solid-state switch device $S_{1-3}$ and the solid-state switch device $S_{1-4}$ are all in the turn-on state when the first voltage is 500 V, the voltage of the end of the capacitor $C_{1-1}$ that is connected to the positive electrode of the first power supply U1 is 2000 V. At this time, the voltage difference between the two ends of the diode $D_{1-1}$ is 1500 V, and it is thus necessary to provide two diodes $D_{1-1}$.

Similarly, if the second voltage is 1000 V, the ground level is 0 V, and the reverse breakdown voltage of each diode is 1100 V, and when the solid-state switch device $S_{2-1}$, the solid-state switch device $S_{2-2}$ and the solid-state switch device $S_{2-3}$ are all in the turn-on state, the voltage of the end of the capacitor $C_{2-1}$ that is connected to the positive electrode of the second power supply U2 is 3000 V. At this time, the voltage difference between two ends of the diode $D_{3-1}$ is 2000 V, and it is thus necessary to provide two diodes $D_{3-1}$.

Referring to FIG. 3, the pulse generation circuit in the embodiments of the present application may further include a first discharge module 4 and a second discharge module 5. The first discharge module 4 is electrically connected to the first pulse generation module and the ground, respectively, and is configured to connect the first pulse generation module to the ground under the control of a first discharge signal to release residual electricity in the first pulse generation module. The second discharge module 5 is electrically connected to the second pulse generation module and the ground, respectively, and is configured to connect the second pulse generation module to the ground under the control of a second discharge signal to release residual electricity in the second pulse generation module.

In some embodiments, the pulse generation circuit may further include a trigger unit 61 and at least a pair of electrodes 62 electrically connected to the trigger unit 61. The trigger unit 61 is electrically connected to the first pulse generation module and the second pulse generation module, respectively, and the electrodes 62 are used for being in contact with the load 3. The trigger unit 61 is configured to turn on when being triggered by a trigger instruction, so that the first pulse signal and/or the second pulse signal are transmitted to the electrodes 62.

In some embodiments, the pulse generation circuit further include an associated switch 63 associated with the trigger unit 61. Specifically, when the synergistic pulse generation circuit in the present embodiment is applied to medical instruments, e.g., an electroablation device, the associated switch 63 may be a foot switch.

In some embodiments, there may be a plurality of pairs of electrodes 62. The pulse generation circuit further includes a multiplexer unit 64, which may convert a signal into multiple of signals so as to match the plurality of pairs of electrodes. Each pair of electrodes 62 need two identical signals.

In some embodiments, the pulse generation circuit further includes a monitoring module, which is used for monitoring voltages outputted by the first pulse signal and/or the second pulse signal and/or monitoring outputted currents of the first pulse signal and/or the second pulse signal. The monitoring module may include a resistor 7, a first monitoring unit 81 and a second monitoring unit 82. The resistor 7 is electrically connected to the first pulse generation module, the second pulse generation module and the ground, respectively, and the first pulse signal and/or the second pulse signal are/is applied to the resistor 7. The first monitoring unit 81 is configured to monitor currents of the first pulse signal and/or the second pulse signal. The second monitoring unit 82 is configured to monitor voltages applied to the resistor 7 by the first pulse signal and/or the second pulse signal. Certainly, it is also possible to use one of the monitoring units to monitor one of a voltage or a current outputted by a synergistic pulse signal. For example, only the first monitoring unit 81 is used, and in this case, the first monitoring unit 81 may be configured to be a voltage sensor or a current sensor.

The first monitoring unit 81 includes a first Pearson coil, and the second monitoring unit 82 includes a second Pearson coil. The first Pearson coil is configured to sense the currents of the first pulse signal and/or the second pulse signal, and the second Pearson coil is configured to sense the voltages applied to the resistor 7 by the first pulse signal and/or the second pulse signal, thereby realizing monitoring of the currents and voltages outputted by the first pulse signal and/or the second pulse signal.

In a particular embodiment, a first pulse signal and a second pulse signal having certain parameters are formed. The two Pearson coils above may sense the corresponding currents and voltages. When sensing results of the two Pearson coils above conform to the parameters of the first pulse signal and the second pulse signal, it is determined that the synergistic pulse generation circuit at this time is in a normal operation state; and once the sensing results of the two Pearson coils above deviate from the parameters of the first pulse signal and the second pulse signal, it is determined that the synergistic pulse generation device is in an abnormal operation state. In this way, an operator may find a fault and take corresponding measures in a timely manner.

For example, when the synergistic pulse generation circuit in the present embodiment is applied to the field of medicines, i.e., a pulse therapy instrument, whether or not a first pulse and/or a second pulse that are/is outputted are/is normal may be determined in a timely manner according to the monitoring result provided by the monitoring module, thereby ensuring that an output on the load 3 coordinates with a set output parameter.

Figure 4:
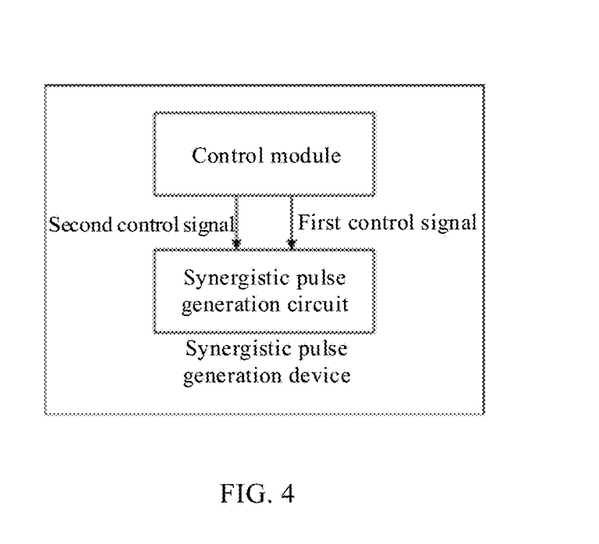
FIG. 4 is a schematic structural diagram of a synergistic pulse generation device provided in an embodiment of the present application.

Based on the same inventive concept, an embodiment of the present application further provides a synergistic pulse generation device. As shown in FIG. 4, the synergistic pulse generation device includes the synergistic pulse generation circuit in the embodiments above and a control module. The control module is electrically connected to the first pulse generation module 1 and the second pulse generation module 2, respectively, and is configured to generate a first control signal and a second control signal according to input information, transmit the first control signal to the first pulse generation module 1, and transmit the second control signal to the second pulse generation module 2.

The synergistic pulse generation device provided by the present embodiment has the beneficial effects of the synergistic pulse generation circuit in the embodiments above, which will not be described in details here.

Specifically, the synergistic pulse generation device in the present embodiment may be used in an electroablation device, which may provide a synergistic output of a microsecond pulse and a nanosecond pulse, and may also be referred to as a micro-nano knife device. For example, the first pulse is a microsecond pulse, and the second pulse is a nanosecond pulse. By means of the micro-nano knife system, a combination of a nanosecond pulse and a microsecond pulse may be generated; and when the combination of the nanosecond pulse and the microsecond pulse is applied to a tumor tissue, the ablation effect on the tumor tissue may be effectively improved.

Figure 5:
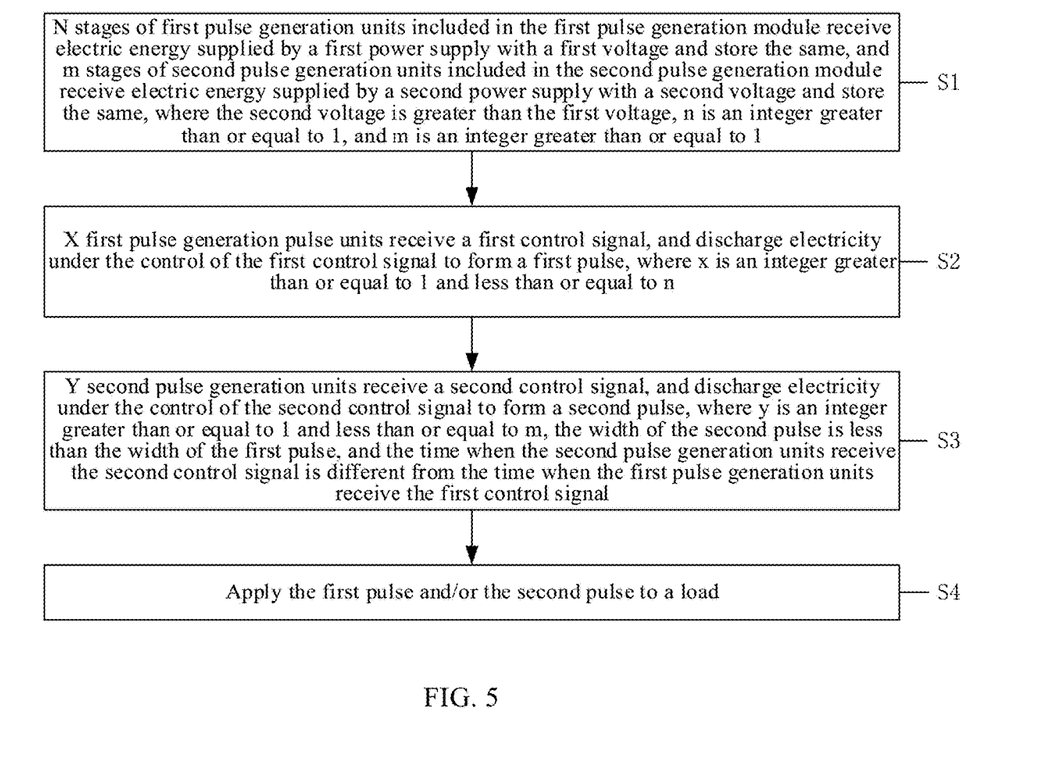
FIG. 5 is a schematic diagram of a flow of a synergistic pulse generation method provided in an embodiment of the present application.

Based on the same inventive concept, an embodiment of the present application further provides a synergistic pulse generation method. As shown in FIG. 5, the synergistic pulse generation method includes steps S1 to S4.

In step S1, n stages of first pulse generation units 11 included in a first pulse generation module 1 receive electric energy supplied by a first power supply U1 with a first voltage and store the same, and m stages of second pulse generation units 21 included in a second pulse generation module 2 receive electric energy supplied by a second power supply U2 with a second voltage and store the same, where the second voltage is greater than the first voltage, n is an integer greater than or equal to 1, and m is an integer greater than or equal to 1.

It should be noted that a charging process of the first pulse generation module 1 and a charging process of the second pulse generation module 2 may be conducted simultaneously, and it is also possible to only charge the first pulse generation module 1 or the second pulse generation module 2, or that the charging process of the first pulse generation module 1 and the charging process of the second pulse generation module 2 are conducted asynchronously.

Specifically, the n stages of the first pulse generation units 11 included in the first pulse generation module 1 receiving the electric energy supplied by the first power supply U1 with the first voltage and storing the same includes: the first switch units 112 are turned off when receiving a third control signal, so that the stages of first storage units 111 are connected to the first power supply U1 in parallel to receive the electric energy supplied by the first power supply U1 and store the same.

Taking the synergistic pulse generation circuit shown in FIG. 3 as an example, the charging process of the first pulse generation module 1 is as follows: when the solid-state switch device $S_{1\text{-}1}$, the solid-state switch device $S_{1\text{-}2}$, the solid-state switch device $S_{1\text{-}3}$ and the solid-state switch device $S_{1\text{-}4}$ receive a third control signal, the solid-state switch device $S_{1\text{-}1}$, the solid-state switch device $S_{1\text{-}2}$, the solid-state switch device $S_{1\text{-}3}$ and the solid-state switch device $S_{1\text{-}4}$ are all in a turn-off state; the diode $D_{1\text{-}1}$, the diode $D_{1\text{-}2}$, the diode $D_{1\text{-}3}$ and the diode $D_{1\text{-}4}$, and the diode $D_{2\text{-}1}$, the diode $D_{2\text{-}2}$, the diode $D_{2\text{-}3}$ and the diode $D_{2\text{-}4}$ all have an unidirectional conduction function, such that the capacitor $C_{1\text{-}1}$, the capacitor $C_{1\text{-}2}$, the capacitor $C_{1\text{-}3}$ and the capacitor $C_{1\text{-}4}$ have a parallel connection relationship and are all electrically connected to a first end and a second end of the first power supply U1, i.e., all being electrically connected to the positive electrode and the negative electrode of the first power supply U1. The charging of the first pulse generation module 1 is completed until the potential difference between two ends of each of the capacitor$_{1\text{-}1}$, the capacitor $C_{1\text{-}2}$, the capacitor $C_{1\text{-}3}$ and the capacitor $C_{1\text{-}4}$ is the first voltage.

Specifically, the m stages of the second pulse generation units 21 included in the second pulse generation module 2 receiving the electric energy supplied by the second power supply U2 with the second voltage and storing the same includes: the second switch units 212 are turned off when receiving a fourth control signal, so that the stages of the second storage units 211 are connected to the second supply U2 in parallel to receive the electric energy supplied by the second power supply U2 and store the same.

Taking the synergistic pulse generation circuit shown in FIG. 3 as an example, the charging process of the second pulse generation module 2 is as follows: when the solid-state switch device $S_{2\text{-}1}$, the solid-state switch device $S_{2\text{-}2}$ and the solid-state switch device $S_{2\text{-}3}$ receive a fourth control signal, the solid-state switch device $S_{2\text{-}1}$, the solid-state switch device $S_{2\text{-}2}$ and the solid-state switch device $S_{2\text{-}3}$ are all in the turn-off state; the diode $D_{3\text{-}1}$, the diode $D_{3\text{-}2}$, the diode $D_{3\text{-}3}$ and the diode $D_{3\text{-}4}$, and the diode $D_{4\text{-}1}$, the diode $D_{42}$ and the diode $D_{4\text{-}3}$ all have an unidirectional conduction function, such that the capacitor $C_{2\text{-}1}$, the capacitor $C_{2\text{-}2}$ and the capacitor $C_{2\text{-}3}$ have a parallel connection relationship and are all electrically connected to a first end and a second end of the second power supply U2, i.e., all being electrically connected to the positive electrode and the negative electrode of the second power supply U2. The charging of the second pulse generation module 2 is completed until the potential difference between two ends of each of the capacitor $C_{2\text{-}1}$, the capacitor $C_{2\text{-}2}$ and the capacitor $C_{2\text{-}3}$ is the second voltage.

In a particular embodiment, the first control signal and the second control signal are both at a high level, and the third control signal and the fourth control signal are both at a low level. That is, as long as the first pulse generation module 1 does not receive the first control signal, the first power supply U1 is in the state of charging the stages of the first capacitors or the state of maintaining the voltage difference between two ends of each stage of the first capacitor to be the first voltage. Similarly, as long as the second pulse generation module 2 does not receive the second control signal, the second power supply U2 is in the state of charging the stages of the second capacitors or the state of maintaining the voltage difference between two ends of each stage of the second capacitor to be the second voltage.

In the step S2, x of the first pulse generation pulse units 11 receive the first control signal, and discharge electricity under the control of the first control signal to form a first pulse applied to a load 3, where x is an integer greater than or equal to 1 and less than or equal to n.

Specifically, as shown in FIG. 5, the first pulse generation units 11 each includes a first storage unit 111, a first switch unit 112 and a first cutoff unit 113. Each of the first cutoff units 113 only allows a current to flow from the first power supply U1 to the first pulse generation unit 11 or from the current stage of the first pulse generation unit 11 to the next stage of a first pulse generation unit 11. At this time, step S2 includes: x of the first switch units 112 receiving the first control signal and being turned on under the control of the first control signal, so that x of the first storage units 111 at the same stages as those of the first switch units 112 receiving the first control signal are connected in series and discharge electricity so as to form the first pulse.

Specifically, as shown in FIG. 3, the first cutoff units 113 each includes a first cutoff device and a second cutoff device. The first storage units 111 each includes a first capacitor, and the first switch units 112 each includes a first solid-state switch device. The first cutoff devices each includes a first diode, and the second cutoff devices each includes a second diode. In the synergistic pulse generation circuit, the first pulse generation module 1 includes four stages of the first pulse generation units 11, that is, n is equal to 4.

As shown in FIG. 3, the first to fourth stages of the first switch units 112, i.e., the first to fourth stages of the first solid-stage switch devices, are respectively a solid-state switch device $S_{1-1}$, a solid-state switch device $S_{1-2}$, a solid-state switch device $S_{1-3}$ and a solid-state switch device $S_{1-4}$. The first to fourth stages of the first switch storages, i.e., the first to fifth stages of the first capacitors, are respectively a capacitor $C_{1-1}$, a capacitor $C_{1-2}$, a capacitor $C_{1-3}$ and a capacitor $C_{1-4}$. The first to fourth stages of the first cutoff devices, i.e., the first to fourth stages of the first diodes, are respectively a diode $D_{1-1}$, a diode $D_{1-2}$, a diode $D_{1-3}$ and a diode $D_{1-4}$. The first to fourth stages of the second cutoff devices, i.e., the first to fourth stages of the second diodes, are respectively a diode $D_{2-1}$, a diode $D_{2-2}$, a diode $D_{2-3}$ and a diode $D_{2-4}$.

As shown in FIG. 3, when the solid-state switch device $S_{1-1}$, the solid-state switch device $S_{1-2}$, the solid-state switch device $S_{1-3}$ and the solid-state switch device $S_{1-4}$ all receive the first control signal, the solid-state switch device $S_{1-1}$, the solid-state switch device $S_{1-2}$, the solid-state switch device $S_{1-3}$ and the solid-state switch device $S_{1-4}$ are all in a turn-on state. Since the diode $D_{1-1}$, the diode $D_{1-2}$, the diode $D_{1-3}$ and the diode $D_{1-4}$, and the diode $D_{2-1}$, the diode $D_{2-2}$, the diode $D_{2-3}$ and the diode $D_{2-4}$ all have the unidirectional conduction function, the capacitor $C_{1-1}$, the capacitor $C_{1-2}$, the capacitor $C_{1-3}$ and the capacitor $C_{1-4}$ have a serial connection relationship, and the capacitor $C_{1-1}$, the capacitor $C_{1-2}$, the capacitor $C_{1-3}$ and the capacitor $C_{1-4}$ discharge electricity simultaneously, with the discharge voltages all being the first voltage, such that the voltage of the formed pulse is four times of the first voltage.

In the step S3, y of the second pulse generation units 21 receive a second control signal, and discharge electricity under the control of the second control signal to form a second pulse applied to the load 3, where y is an integer greater than or equal to 1 and less than or equal to m. The width of the second pulse is less than the width of the first pulse, and the time when the second pulse generation units 21 receive the second control signal is different from the time when the first pulse generation units 11 receive the first control signal.

Specifically, as shown in FIG. 5, the second pulse generation units 21 each includes a second storage unit 211, a second switch unit 212 and a second cutoff unit 213. Each of the second cutoff units 213 only allows a current to flow from the second power supply U2 to the second pulse generation unit 21 or from the current stage of the second pulse generation unit 21 to the next stage of a second pulse generation unit 21. At this time, step S3 includes: y of the second switch units 212 receiving the second control signal and being turned on under the control of the second control signal, so that y of the second storage units 211 at the same stage as those of the second switch units receiving the second control signal are connected in series and discharge electricity so as to form the second pulse.

Specifically, as shown in FIG. 3, the second cutoff units 213 each includes a third cutoff device and a fourth cutoff device. The second storage units 211 each includes a second capacitor. The second switch units 212 each includes a second solid-state switch device. The third cutoff devices each includes a third diode, and the fourth cutoff devices each includes a fourth diode. In the synergistic pulse generation circuit, the second pulse generation module 2 includes three stages of second pulse generation units 21, that is, m is equal to 3.

As shown in FIG. 3, the first to third stages of the second switch units 212, i.e., the first to third stages of the second triodes, are respectively a solid-state switch device $S_{2-1}$, a solid-state switch device $S_{2-2}$ and a solid-state switch device $S_{2-3}$. The first to third stages of the second storage units 211, i.e., the first to third stages of the second capacitors, are respectively a capacitor $C_{2-1}$, a capacitor $C_{2-2}$ and a capacitor $C_{2-3}$. The first to third stages of the third cutoff devices, i.e., the first to third stages of the third diodes, are respectively a diode $D_{3-1}$, a diode $D_{3-2}$ and a diode $D_{3-3}$. The first to third stages of the fourth cutoff devices, i.e., the first to third stages of the fourth diodes, are respectively a diode $D_{4-1}$, a diode $D_{42}$ and a diode $D_{4-3}$.

As shown in FIG. 3, when the solid-state switch device $S_{2-1}$, the solid-state switch device $S_{2-2}$ and the solid-state switch device $S_{2-3}$ all receive the second control signal, the solid-state switch device $S_{2-1}$, the solid-state switch device $S_{2-2}$ and the solid-state switch device $S_{2-3}$ are all in the turn-on state, the capacitor $C_{2-1}$, the capacitor $C_{2-2}$ and the capacitor $C_{2-3}$ have the serial connection relationship, and the capacitor $C_{2-1}$, the capacitor $C_{2-2}$ and the capacitor $C_{2-3}$ discharge electricity simultaneously, with the discharge voltages all being the second voltage, such that the voltage of the formed second pulse is three times of the second voltage.

In the step S4, the first pulse and/or the second pulse are applied to the load 3.

By means of the synergistic pulse generation method provided in the present embodiment, it is possible to selectively form a first pulse and a second pulse of different widths, and select the voltages of the first pulse and the second pulse, so as to achieve the purpose of applying a combination pulse to a load 3. Taking the load 3 being tumor cells as an example, the action of the combination pulse is conducive to an improvement in the ablation effect on the tumor cells.

It should be noted that the synergistic pulse generation method provided by the present embodiment may only include one of step S1 and step S2, and may also include both of step S1 and step S2. Moreover, the sequence of step S1 and step S2 may be adjusted according to actual needs, that is, different pulse combinations may be outputted according to the actual needs. In a particular embodiment, a pulse combination includes a plurality of first pulse groups, the time interval between two adjacent first pulse groups is t1, each first pulse group includes a first pulse signals, and the time interval between two adjacent first pulse signals is t2. That is, only step S1 among step S1 and step S2 is included. In another particular embodiment, the pulse combination includes a plurality of second pulse groups, the time interval between two adjacent second pulse groups is t3, each second pulse group includes b second pulse signals, and the time interval between two adjacent second pulse signals is t4. That is, only step S2 among step S1 and step S2 is included. In still another particular embodiment, the pulse combination includes a plurality of first pulses and a plurality of second pulses. It is possible to alternately apply the first pulses and the second pulses to the load 3. It is also possible to apply the second pulses to the load 3 after all the first pulses have been applied to the load 3, or apply the first pulses to the load 3 after all the second pulses have been applied to the load 3. It is also possible to combine these first pulses into a plurality of first pulse groups and combine these second pulses into a plurality of second pulse groups, and alternately apply the first pulse groups and the second pulse groups to the load 3. That is, both step S1 and step S2 are included.

By means of the embodiments of the present application, at least the following beneficial effects may be achieved: by means of the synergistic pulse generation circuit, generation device and generation method therefor provided by the embodiments of the present application, it is possible to selectively form a first pulse and/or a second pulse of different widths, and select the voltages of the first pulse and the second pulse, so as to achieve the purpose of applying a combination pulse to a load. Taking the load being tumor cells as an example, the action of the combination pulse is conducive to an improvement in the ablation effect on the tumor cells.

The terms "first" and "second" are used for descriptive purposes only, and cannot be construed as indicating or implying relative importance or implicitly indicating the number of technical features indicated. Thus, the features defined with "first" and "second" may explicitly or implicitly include one or more features. In the description of the present application, unless otherwise specified, "a plurality of" means two or more.

In the description of the present application, it should be noted that, unless otherwise explicitly specified and defined, the terms "mounting", "connecting" and "connection" should be understood in a broad sense, for example, they may be a fixed connection, a detachable connection, or an integrated connection; and may be directly connected, or indirectly connected by means of an intermediate medium, or communication between interiors of two elements. For those of ordinary skill in the art, the specific meaning of the terms mentioned above in the present application may be construed according to specific circumstances.

In the description of the present specification, the specific features, structures, materials or characteristics may be combined in a suitable manner in any one or more embodiments or examples.

The above merely describes some embodiments of the present application, and it should be noted that for persons of ordinary skill in the art, several improvements and modifications may also be made without departing from the principle of the present application, and these improvements and modifications are also considered to be within the scope of protection of the present application.

What is claimed is:

1. A synergistic pulse generation circuit, comprising:
a first power supply;
a first pulse generation module electrically connected to the first power supply, wherein the first pulse generation module comprises n stages of first pulse generation units, each of which is configured to receive electric energy supplied by the first power supply with a first voltage and store the same, and release the stored electric energy when receiving a first control signal, so that x of the first pulse generation units receiving the first control signal discharge electricity to form a first pulse applied to a load, where n is an integer greater than or equal to 1, and x is an integer greater than or equal to 1 and less than n;
a second power supply; and
a second pulse generation module electrically connected to the second power supply, wherein the second pulse generation module comprises m stages of second pulse generation units, each of which is configured to receive electric energy supplied by the second power supply with a second voltage and store the same, and release the stored electric energy when receiving a second control signal, so that y of the second pulse generation units receiving the second control signal discharge electricity to form a second pulse applied to the load, where m is an integer greater than or equal to 1, and y is an integer greater than or equal to 1 and less than m, wherein output ends of the first pulse generation module and the second pulse generation module are configured to connect to the same load, the second voltage is greater than the first voltage, and a width of the second pulse is less than a width of the first pulse.

2. The synergistic pulse generation circuit according to claim 1, wherein
the first pulse generation units each comprises a first storage unit, a first switch unit and a first cutoff unit,
wherein the first switch units are configured to receive the first control signal and turn on under the control of the first control signal, so that the respective first storage units at the same stages as those of the first switch units receiving the first control signal are connected in series and discharge electricity so as to form the first pulse, and
each of the first cutoff units is configured to only allow a charging current to flow from the first power supply to a corresponding one of the first pulse generation units or flow from a current stage of the first pulse generation unit to a next stage of the first pulse generation unit, and only allow a discharging current to flow from the current stage of the first pulse generation unit to the next stage of the first pulse generation unit; and
the second pulse generation units each comprises a second storage unit, a second switch unit and a second cutoff unit,
wherein the second switch units are configured to receive the second control signal and turn on under the control of the second control signal, so that the respective second storage units at the same stages as those of the second switch units receiving the second control signal are connected in series and discharge electricity so as to form the second pulse, and
each of the second cutoff units is configured to only allow a charging current to flow from the second power supply to a corresponding one of the second pulse generation units or flow from a current stage of the second pulse generation unit to a next stage of the second pulse generation unit, and only allow a discharging current to flow from the current stage of the second pulse generation unit to the next stage of the second pulse generation unit.

3. The synergistic pulse generation circuit according to claim 2, wherein
the first switch units are further configured to turn off when receiving a third control signal, so that stages of the first storage units are connected to the first power supply in parallel to receive electric energy supplied by the first power supply and store the same; and
the second switch units are further configured to turn off when receiving a fourth control signal, so that stages of the second storage units are connected to the second power supply in parallel to receive electric energy supplied by the second power supply and store the same.

4. The synergistic pulse generation circuit according to claim 2, wherein
the first cutoff units each comprises a first cutoff device and a second cutoff device, a first-stage of the first cutoff device is electrically connected to a first end of the first power supply and a first end of a first-stage of the first storage unit, respectively, an ith-stage of the first cutoff device is electrically connected to a first end of an (i−1)th-stage of the first storage unit, a first end of an ith-stage of the first storage unit and an (i−1)th-stage of the first cutoff device, respectively, each stage of the second cutoff device is electrically connected to a second end of a current stage of the first storage unit, a second end of a current stage of the first switch unit and a next stage of the second cutoff device, respectively, where i is an integer greater than or equal to 2; and the second cutoff units each comprises a third cutoff device and a fourth cutoff device, a first-stage of the third cutoff device is electrically connected to a first end of the second power supply and a first end of a first-stage of the second storage unit, respectively, a jth-stage of the third cutoff device is electrically connected to a first end of a (j−1)th-stage of the second storage unit, a first end of a jth-stage of the second storage unit and a (j−1)th-stage of the third cutoff device, respectively, each stage of the fourth cutoff device is electrically connected to a second end of a current stage of the second storage unit, a second end of a current stage of the second switch unit and a next stage of the fourth cutoff device, respectively, where j is an integer greater than or equal to 2.

5. The synergistic pulse generation circuit according to claim 4, wherein
two ends of each stage of the first storage unit are electrically connected to two ends of the first power supply, respectively, a control end of each stage of the first switch unit is configured to receive the first control signal, and the first end and the second end of each stage of the first switch unit are electrically connected to the first end of the current stage of the first storage unit and the second end of a next stage of the first storage unit, respectively; and
two ends of each stage of the second storage unit are electrically connected to two ends of the second power supply, respectively, a control end of each stage of the second switch unit is configured to receive the second control signal, and the first end and the second end of each stage of the second switch unit are electrically connected to the first end of the current stage of the second storage unit and the second end of a next stage of the second storage unit, respectively.

6. The synergistic pulse generation circuit according to claim 4, wherein
the first storage unit comprises a first capacitor, and the second storage unit comprises a second capacitor;
the first switch unit comprises a first solid-state switch device, and the second switch unit comprises a second solid-state switch; and
the first cutoff device comprises a first diode, the second cutoff device comprises a second diode, the third cutoff device comprises a third diode, and the fourth cutoff device comprises a fourth diode.

7. The synergistic pulse generation circuit according to claim 6, wherein
the second to nth stages of the first cutoff devices each comprises one first diode, each stage of the second cutoff device comprises one second diode, and a reverse breakdown voltage of each of the first diodes and a reverse breakdown voltage of each of the second diodes are both greater than the first voltage; and
the second to mth stages of the third cutoff devices each comprises one third diode, each stage of the fourth cutoff device comprises one fourth diode, and a reverse breakdown voltage of each of the third diodes and a reverse breakdown voltage of each of the fourth diodes are both greater than the second voltage.

8. The synergistic pulse generation circuit according to claim 7, wherein
the first-stage of the first cutoff device comprises s first diodes, and s times of the reverse breakdown voltage of the first diode is greater than (n−1) times of the first voltage, where s is an integer greater than or equal to 1; and
the first-stage of the third cutoff device comprises t third diodes, and s times of the reverse breakdown voltage of the third diode is greater than (m−1) times of the second voltage, where t is an integer greater than or equal to 1.

9. The synergistic pulse generation circuit according to claim 1, wherein the pulse generation circuit further comprises:
a first discharge module electrically connected to the first pulse generation module and the ground, respectively, and configured to enable an electrical conduction from the first pulse generation module to the ground under the control of a first discharge signal to release residual electricity in the first pulse generation module; and
a second discharge module electrically connected to the second pulse generation module and the ground, respectively, and configured to enable an electrical conduction from the second pulse generation module to the ground under the control of a second discharge signal to release residual electricity in the second pulse generation module.

10. The synergistic pulse generation circuit according to claim 1, wherein
the first pulse is a millisecond pulse or a microsecond pulse; and
the second pulse is a nanosecond pulse.

11. The synergistic pulse generation circuit according to claim 1, further comprising a trigger unit and at least a pair of electrodes electrically connected to the trigger unit,
wherein the trigger unit is electrically connected to the first pulse generation module and the second pulse generation module, respectively, and the electrodes are used for connecting to the load; and
the trigger unit is configured to turn on when being triggered by a trigger instruction, so that the first pulse signal and/or the second pulse signal are transmitted to the electrodes.

12. The synergistic pulse generation circuit according to claim 1, further comprising:
a monitoring module configured to monitor voltages outputted by the first pulse signal and/or the second pulse signal and monitor output currents of the first pulse signal and/or the second pulse signal.

13. A synergistic pulse generation device, comprising:
a synergistic pulse generation circuit according to claim 1; and
a control module electrically connected to a first pulse generation module and a second pulse generation module, respectively, and configured to generate a first control signal and a second control signal according to input information, transmit the first control signal to the first pulse generation module, and transmit the second control signal to the second pulse generation module.

14. A synergistic pulse generation method for the synergistic pulse generation circuit according to claim 1, the method comprising:
n stages of first pulse generation units included in first pulse generation module receiving electric energy supplied by a first power supply with a first voltage and storing the same, and m stages of second pulse generation units included in second pulse generation module receiving electric energy supplied by a second power supply with a second voltage and storing the same, where n is an integer greater than or equal to 1, m is an integer greater than or equal to 1, and the second voltage is greater than the first voltage;

x of the first pulse generation pulse units receiving a first control signal, and discharging electricity under the control of the first control signal to form a first pulse, where x is an integer greater than or equal to 1 and less than n;

y of the second pulse generation units receiving a second control signal, and discharging electricity under the control of the second control signal to form a second pulse, where y is an integer greater than or equal to 1 and less than m; and applying the first pulse and/or the second pulse to a load, wherein a width of the second pulse is less than a width of the first pulse.

15. The synergistic pulse generation method according to claim 14, wherein
a time when the second pulse generation units receive the second control signal is different from a time when the first pulse generation units receive the first control signal.

16. The synergistic pulse generation method according to claim 14, wherein
the first pulse generation units each comprises a first storage unit, a first switch unit and a first cutoff unit, the first cutoff unit only allowing a current to flow from the first power supply to a corresponding one of the first pulse generation units or from a current stage of the first pulse generation unit to a next stage of the first pulse generation unit;
the x of the first pulse generation pulse units receiving the first control signal and discharging electricity under the control of the first control signal to form the first pulse comprises: x of the first switch units receiving the first control signal and being turned on under the control of the first control signal, so that x of the first storage units at the same stages as those of the first switch units receiving the first control signal are connected in series and discharge electricity so as to form the first pulse;
the second pulse generation units each comprises a second storage unit, a second switch unit and a second cutoff unit, the second cutoff unit only allowing a current to flow from the second power supply to a corresponding one of the second pulse generation units or from a current stage of the second pulse generation unit to a next stage of the second pulse generation unit; and
the y of the second pulse generation units receiving the second control signal and discharging electricity under the control of the second control signal to form the second pulse comprises: y of the second switch units receiving the second control signal and being turned on under the control of the second control signal, so that y of the second storage units at the same stages as those of the second switch units receiving the second control signal are connected in series and discharge electricity so as to form the second pulse.

17. The synergistic pulse generation method according to claim 16, wherein
the n stages of the first pulse generation units included in the first pulse generation module receiving the electric energy supplied by the first power supply with the first voltage and storing the same comprises: the first switch units being turned off when receiving a third control signal, so that the stages of the first storage units are connected to the first power supply in parallel to receive the electric energy supplied by the first power supply and store the same; and
the m stages of the second pulse generation units included in the second pulse generation module receiving the electric energy supplied by the second power supply with the second voltage and storing the same comprises: the second switch units being turned off when receiving a fourth control signal, so that the stages of the second storage units are connected to the second supply in parallel to receive the electric energy supplied by the second power supply and store the same.

18. The synergistic pulse generation method according to claim 14, wherein
the first pulse is a millisecond pulse or a microsecond pulse; and
the second pulse is a nanosecond pulse.

* * * * *